United States Patent
Poruban et al.

(10) Patent No.: US 7,074,609 B2
(45) Date of Patent: Jul. 11, 2006

(54) CLAVARIA FUNGUS

(76) Inventors: Richard Poruban, 38029 Detroit Rd., Avon, OH (US) 44011-2162; Floyd R. Poruban, 38029 Detroit Rd., Avon, OH (US) 44011-2162

( * ) Notice: Subject to any disclaimer, the term of this patent is extended or adjusted under 35 U.S.C. 154(b) by 320 days.

(21) Appl. No.: 10/246,564

(22) Filed: Sep. 18, 2002

(65) Prior Publication Data

US 2004/0053400 A1  Mar. 18, 2004

Related U.S. Application Data

(60) Provisional application No. 60/322,618, filed on Sep. 17, 2001.

(51) Int. Cl.
*C12N 1/14* (2006.01)
*A01N 65/00* (2006.01)

(52) U.S. Cl. .................................. 435/254.1; 424/93.5

(58) Field of Classification Search ............. 435/254.1, 435/252.1; 424/93.5
See application file for complete search history.

(56) References Cited

OTHER PUBLICATIONS http://mycology.couchconservancy.ca/details.asp?groupNum=6&Species=laeticolor&Genus=Ramariopsis&pID=469 "Genus: *Ramariopsis* Species: *laeticolor*".*
Petersen Mycologia 57:522. 1965. http://www.mykoweb.com/CAF/species/Clavulinopsis_laeticolor.html.*
http://www.bluewillowpages.com/mushroomexpert/clavulinopsis_laeticolor.html "Synonyms".*

* cited by examiner

Primary Examiner—Herbert J. Lilling
(74) Attorney, Agent, or Firm—McDonald Hopkins Co.

(57) ABSTRACT

The present invention is directed to an isolated *Clavaria pulchra* fungus from basidiocarps. The *Clavaria pulchra* fungus can be propagated to ericaceous plants for growth stimulation. The present invention is also directed to a method for isolating Clavarioid fungi.

4 Claims, No Drawings

CLAVARIA FUNGUS

This application claims priority from U.S. Application Ser. No. 60/322,618, filed on Sep. 17, 2001.

FIELD OF INVENTION

The present invention is directed to an isolated coral fungus identified as *Clavaria pulchra*. The present invention is also directed to a method for isolating clavarioid fungi.

BACKGROUND OF THE INVENTION

The *Clavaria* species of fungi varies greatly in form and size from very small simple clubs or rods to large coral-like masses weighing several pounds. Most of the larger and a number of the smaller *Clavaria* species grow on the ground, but many species grow on rotting leaves or wood. A stem, if present, is not sharply marked off as a rule from the spore-bearing part of the *Clavaria*, but is usually sterile, as is shown under a lens by the appearance of its surface, which is different from the more waxy hymenium. In a few *Clavaria* species, however, the stem is distinctly indicated by a different color, or an abrupt reduction in size, or by both. Most of the *Clavaria* species are tender and may be used for food if large enough, but vary decidedly in palatability and some *Clavaria* species are apparently unwholesome.

*Clavaria pulchra*, a particular species in the *Clavaria* family, is generally described in Coker, *The Club and Coral Mushrooms (Clavarias) of the United States and Canada*, p. 58 (repub. 1974, Dover Pub., Inc.), as plants gregarious, mostly cespitose in clusters of several to about twenty, often single or in twos and threes, not densely fascicled or fused at base in large groups as in *Clavaria fusiformis* or *Clavaria fumosa*, but several individuals may be so fused. *Clavaria pulchra* is generally about 1.5–7.4 cm high and 1.2–6 mm thick near the top. *Clavaria pulchra* is long club-shaped or nearly cylindrical, at times compressed and grooved, and tapering downward. The stem of the *Clavaria pulchra* is not distinct from the club, except for decidedly lighter color usually, and the base can be incrassated. The apex is bluntly rounded and not apiculate. The surface is smooth and generally has an egg-yellow color, while the base and at times the apex is lighter, although at times the apex may be darker. The flesh of the *Clavaria pulchra* is toughish, elastic, may crack but not snap when bent at a 45° angle, stuffed or varying to imperfectly or distinctly hollow at maturity. *Clavaria pulchra* generally taste sweetish and pleasant and does not have an odor.

Spores of *Clavaria pulchra* are white, oblong-ovoid with a prominent mucro on one side near the large end, usually with a distinct oil drop, 4.6×6–7μ. Basidia (in dried plants) are about 5–7μ thick, 4-spored, and smaller than in *Clavaria fusiformis*.

*Clavaria pulchra* is nearest to *Clavaria fusiformis*, which normally differs in larger size, fasciculate habit, strong taste and different spores. Separate plants of the latter, which are often found among colonies of cespitose ones, are distinguished from *Clavaria pulchra* by their company, their spores, and their bitter or farinaceous taste. From *Clavaria helveola*, *Clavaria pulchra* is easily distinguished by the deeper color, and the very different spores. The spores of *Clavaria helveola* are smooth, 4.5×6–6.8μ, and are shaped as in *Clavaria pulchra*. *Clavaria similes* have strongly warted spores.

To date, *Clavaria pulchra* has not been successfully isolated and reproduced in a controlled setting. It would be beneficial to isolate and reproduce *Clavaria pulchra* so that the *Clavaria pulchra* may enter into a mycorrhizal relationship with a plant, and the plant may obtain increased water and nutrients upon entering a mycorrhizal relationship with *Clavaria pulchra*.

SUMMARY OF INVENTION

The present invention is directed to an isolated *Clavaria pulchra* fungus. The present invention is also directed to an agricultural composition for plant growth comprising an effective amount of *Clavaria pulchra* fungus. The present invention is further directed to a biologically pure mycelium of *Clavaria pulchra* fungus. In addition, the present invention is directed to a mycorrhiza comprising a biologically pure *Clavaria pulchra* fungus and an ericaceous plant propagated to the fungus.

The present invention is also directed to a method for isolating clavarioid fungi. The method includes the step of selecting basidiocarps at a proper developmental stage. The method further includes sterilizing the basidiocarps. The method further includes the step of plating the basidiocarps on an ericaceous leaf medium.

DETAILED DESCRIPTION OF THE PREFERRED EMBODIMENTS

*Clavaria* is a basidiomycete that includes a basidium-bearing structure known as a basidiocarp. Basidiocarp height ranges from 2.5–9 cm, with average height between 5–6 cm and width between 3–6 mm. They are yellow and club-shaped and occur predominantly in clusters, although sometimes may occur singly. Basidiocarps are brittle and snap when bent beyond 45° and feel waxy and smooth to the touch. They have a subtle taste and have almost no odor.

An isolated and biologically pure culture of *Clavaria* fungus has been deposited having the NRRL Accession number 30874.

*Clavaria pulchra* is a member of the *Clavaria* family. Over the years, taxonomists have used numerous names to describe the *Clavaria pulchra* fungus including, but not limited to *Clavaria laeticolor, Clavaria persimilis, Clavulinopsis pulchra, Clavulinopsis laeticolor*, and *Clavaria thymiphila*. More recently, some literature has named the *Clavaria pulchra* fungus *Clavulinopsis laetevirens*. Each of the above-mentioned nomenclature, however, names the *Clavaria pulchra* fungus.

Based upon observation by the present inventors, *Clavaria pulchra* basidiocarps typically initiate about 3 days before the full moon in October and are at near maximum height by the October full moon. Fruiting continues from October until the ground freezes. *Clavaria pulchra* sporulates annually whether or not the ground has been disturbed. Initiation time observations rigidly followed the lunar cycle in 1999 and 2000 when the full moons were on October 24, and October 13 respectively, but the timing of the first frost and the amount of soil organic matter apparently play a role in basidiocarp formation under certain circumstances.

For Example, in 2001, October had two full moons. The first full moon was on October 2, however, basidiocarp formation around azaleas, planted where soil ground had little visible organic matter, was not observed until October 9. The frost was on October 7, and basidiocarps were measured to be 1/8" to 3/16" tall on October 9 at about two days old. The frost was on October 7.

On Oct. 12, 2001, fully formed basidiocarps were noted under Rhododendron "Roseum Elegans" where large amounts of visible organic material existed. Though *Clavaria* basidiocarps normally reach maximum height by the full moon, fully formed basidiocarps take about 7–10 days to fully mature, persist for 3–4 more days, and then begin to senesce in cool October weather. This timeline supports lunar initiation of *Clavaria* fruiting.

The interplay of organic material and frost must be researched more fully to determine their effects. It is possible that the frost has some effect on the availability of iron, used by plant roots to detect gravitation, in soil depleted of organic matter after droughty conditions that were present in 2001. The organic matter noted under the rhododendrons may contain more available iron, which would allow basidiocarp formation to follow the lunar cycle closely.

Basidiocarps occur in partial shade only around plants of the Ericaceae family. Basidiocarps are observed in the Ericaceae family genera including, but not limited to: *Andromeda; Arbutus; Arctostaphylos; Bruckenthalia; Calluna; Camellia; Chamaedaphne; Daboecia; Elliottia; Enkianthus, Epigea, Erica; Gaultheria; Gaylusaccia; Kalmia; Ledum; Leiophyllum; Leucothoe; Lyonia; Pieris; Rhododendron* (including lepidotes, elepidotes, and azaleas); *Vaccinium*; and *Zenobia*. Fruiting does not occur in full sun or in deep shade, but it usually occurs around the east and north sides of plants within the drip line in partial shade, although shade from surrounding plants may allow it on the south and west sides. *Clavaria pulchra* generally grows among leaf litter or moss outcroppings, but always grows from the soil and not the litter or the outcroppings. *Clavaria pulchra* also grows out of soil on the sides of holes where the roots of established plants were exposed.

Lichens are quite common on and around the plants where *Clavaria pulchra* grows. Many of the lichens have fruiting structures that resemble *Clavaria* basidiocarps in shape and configuration. The lichens commonly grow proximally to species of *Clavicorona*, a closely related genus that grows on the leaf litter.

Plants surrounded by basidiocarps are usually well branched and vigorous with few, if any, disease problems. They appear to be more drought resistant and cold tolerant compared to plants in other areas of the same field where the basidiocarps have not been seen. All areas where *Clavaria pulchra* has been observed have been nutrient poor acid sands along an ancient beach ridge of Lake Erie.

Although fruiting of *Clavaria pulchra* has been observed only around plants of the Ericaceae family, *Clavaria pulchra* may also survive on an alternate host or on soil organic matter. Pin Cherry, Pin Oak, Malus spp., grasses, Multiflora Roses, blackberries, other ornamental crops, mosses, and lichens are in the proximity to the plants where the fruiting has occurred. Another species of *Clavaria, Clavaria vermiculata*, also referred to as *Clavaria vermicularis*, has been seen fruiting in disturbed soil and on the side of a ditch where roots of Malus "Red Jewel" were exposed. The fruiting only occurs after soil disturbance and occurs earlier in the year than *Clavaria pulchra*, i.e., around August. Fruiting has been sporadic over several years and is requisite on soil disturbance. No Ericaceae were present in immediate proximity to the Malus where *Clavaria vermiculata* fruited.

The applications of *Clavaria pulchra* and other *Clavarias* and related species are potentially quite numerous: mycorrhizae, generators of compounds for agricultural, industrial, and medical applications, ornamentals, symbionts; genetic, nutrient, and chemical transfer organisms; bioelectrical conduits; plant disease, pest, and physiology manipulators; decomposers; environmental indicator species; and sources of specimens for education, research, and industry.

The *Clavaria pulchra* fungus forms an endotrophic mycorrhiza, or an endomycorrhiza, specifically classed as an ericoid mycorrhiza. In this type of mycorrhiza, the hyphae of the fungus grow into the cells of the plant's roots and form coils. Through the mycelium of the fungus, mycorrhizal roots can gain access to a larger volume of soil than uninfected ones. The surface that is active in taking up nutrients is strongly enlarged, and plant growth hormones are commonly produced. The plant can make better use of both organic and inorganic sources of nitrogen, phosphorus, and other nutrients due to the fungus, even when available soil water is reduced. Preferably, the mycorrhiza comprises a biologically pure *Clavaria pulchra* fungus and an ericaceous plant propagated to the fungus. The ericaceous plant is preferably from the Ericaceae family genera including but not limited to: *Andromeda; Arbutus; Arctostaphylos; Bruckenthalia; Calluna; Camellia; Chamaedaphne; Daboecia; Elliottia; Enkianthus, Epigea, Erica; Gaultheria; Gaylusaccia; Kalmia; Ledum; Leiophyllum; Leucothoe; Lyonia; Monotropa; Pieris; Rhododendron* (including lepidotes, elepidotes, and azaleas); *Vaccinium*; and *Zenobia*.

The isolation and culture process will be immediately useful for conservationists who want to collect rare species and preserve genetic material for posterity and for people to collect specimens to study the organism itself and environmental, agricultural, industrial effects on the organism as well as environmental, agricultural, industrial, medical and culinary effects of the organism.

In addition to *Clavaria pulchra*, other Clavarioid fungi, also known as coral fungi, including *Clavaria vermiculata* and *Clavicorona pyxidata* can also be isolated using the same method used for isolating *Clavaria pulchra*. The method for isolating Clavarioid fungi includes selecting basidiocarps at a proper developmental stage; sterilizing the basidiocarps; and plating the basidiocarps on an ericaceous leaf medium.

The present invention is illustrated in the following Example that is not intended to be limited in scope.

EXAMPLE

Isolation of a Clavarioid Fungus such as *Clavaria pulchra*:

Timing:

*Clavaria pulchra* must be isolated when the basidiocarps are at the correct developmental stage for best success. Collection can be any time between initiation in October and when the ground freezes. Basidiocarps collected before the proper stage often do not sprout and are too small to handle without damage.

Basidiocarps should be fully elongated, plump, and firm without brown tips, deep wrinkles, or damage of any kind. Tips should be yellow like the rest of the basidiocarp. There is often a whitish, waxy-looking bloom on the basidiocarps at the proper stage. The bloom should be intact for best results. *Clavaria* is collected with a ball of soil, so that the clumps of basidiocarps are not disturbed until they are sectioned and prepared for culture. An adequate ball of soil needs not extend more than 3–4 cm around a cluster of basidiocarps. Basidiocarps should be kept in a large plastic container with a lid with at least 10 cm of free air space above the specimens. Basidiocarps may be kept in the refrigerator 3–4 days using this collection method. Smaller containers retain too much humidity as the container environment is cooled and allow contaminants to flourish in as few as 2 days. Basidiocarps picked without the ball of soil dry out rapidly and are not suitable for culture beyond 24 hours. Collection immediately before isolation is best.

Surface Sterilization:

Surface sterilization is critical to the success of isolating *Clavaria pulchra*. Basidiocarps should be free of foreign matter before surface sterilizing. Rinsing under gently running tap water will be sufficient, but should be done only if necessary. Basidiocarps are severed at the soil line and immediately immersed into a container of 10% chlorine bleach solution in a sterile hood. *Clavaria pulchra* basidiocarps are agitated in the bleach solution for 30–45 seconds and then immersed and agitated in three baths of sterile distilled water for about 10 seconds each. For smaller basidiocarps, like *Clavicorona pyxidata*, bleach timing must be determined experimentally but averages 15–25 seconds. Agitation ensures that air bubbles are dislodged and that all surfaces are coated by the bleach solution. Forceps should be flamed between solutions, and all further manipulations should be done with flamed forceps. At this stage of isolation, only the bottom halves of basidiocarps are handled with forceps to prevent damage to the parts used for sectioning. The bottom halves will be discarded.

Sectioning:

After surface sterilization, basidiocarps are placed, using cooled forceps, onto dry sterile paper towels inside the hood to remove excess moisture. Paper towels are the work surface for sectioning. The top centimeter of the basidiocarp gives the most consistent isolation results. 2–3 transverse sections from each basidiocarp can be made with a flamed, cooled scalpel. Longitudinal sections damage the tissue badly, are difficult to handle, and dramatically decrease isolation success. Sections are placed into vessels containing rhododendron leaf extract medium (RLEM). It is noted that other ericaceous leaves may be used as part of the medium instead of rhododendron leaves. Smaller basidiocarps may be used intact except for removal of basal portion damaged by forceps. The vessels are then sealed with Parafilm™ or a plastic wrap that is not too brittle. Vessels are kept at room temperature.

Isolation Medium:

For 1 L of medium:

250 g fresh or fresh-frozen leaves of rhododendron (or any other Ericaceae plant leaf)
15 g Agar
10 g Dextrose
5 g N-soy Peptone
2 g Yeast Extract
0.5 ml potable ethanol (0.662 ml Vodka (75.5% EtOH)) or 0.5 ml Corn Oil
100 mg Gentamycin Sulfate
1 mg Thiamine
27 mg of Iron Glycinate (Human Iron Supplement)
Distilled Water The leaves should be macerated in a food processor before boiling. Rhododendron leaves should be boiled for 1 hour in distilled water. Water is added as necessary to prevent total boil off. The extract is strained with a sieve to remove leaves and then through any suitable paper filter to remove sediment. A drip coffee filter works well, and a suction funnel may be used to hasten the process. The remaining ingredients are added while the mixture is stirred, even while the extract is hot.

The medium is pressure cooked or autoclaved at 15 psi for about 15 minutes. If vessels are to be filled another day, medium may be reheated for an additional 5 minutes to remelt the agar. The total cooking time at 15 psi should be no more than 20 minutes. Overheating the medium may result in caramelizing the sugar and rendering the medium useless. Vessels should be filled as soon as the medium is cool enough to handle safely.

The initial pH of the medium will vary with the rhododendron leaves. *Clavaria pulchra* seems to grow in a wide pH range. The native pH of the medium is apparently sufficient for growth.

Lowering the pH below 4.5 inhibits bacterial growth, but will not inhibit the growth of actinomycetes, yeasts or other fungi. Adjusting the pH to below 4.0 requires the use of HCl or lactic acid before sterilizing. However, just before RLEM is cool enough to pour into culture vessels 1 ml of 85% lactic acid must be added to harden the agar. Vessels must be filled before the medium is cooled because the medium will harden quickly with the addition of 85% lactic acid. Gentamycin sulfate is added to inhibit bacterial growth without unnecessarily lowering the pH. Gentamycin sulfate also inhibits actinomycete growth but not yeast growth.

The addition of thiamine to the medium allows the *Clavaria pulchra* to grow faster than *Aspergillus* spp. Mycelium. Thiamine also delays the onset of, without inhibiting, the sporulation of *Aspergillus* spp., allowing timely replating of *Clavaria pulchra* mycelium to escape contamination.

Alcohol or Corn oil in RLEM is necessary for *Clavaria pulchra* to produce the lipids needed for long-term survival. In a medium devoid of alcohol or corn oil, lipid droplets within the hyphae will shrink and disappear in successive subcultures, and the fungus will die.

Iron in the medium stimulates lush growth and more rapid growth initiation after initial plating and subculturing.

Culture:

One section of the basidiocarp is placed into the center of each vessel. At least 3 mm of the section should protrude above the medium surface. Once plated, the basidiocarp should retain most of its yellow color for about 24–48 hours and then turn into a brown color. After a day or two, a gelatinous yeast coating may appear on the section. The yeast seems to have a stimulatory effect on *Clavaria pulchra* mycelium emergence and benefits isolation.

*Clavaria pulchra* does not grow from the basidiocarp without the yeast present. *Clavaria* mycelium emerges from the basidiocarp, at the earliest, after 1 day in iron-supplemented medium or 2 days in un-supplemented, but no later than 4 days from initial plating. Mycelial growth appearing after 4 days will be a contaminant.

A *Clavaria* hypha has a small diameter resembling ascomycete hyphae, however it is vigorous, forms infrequent clamp connections, and the growth margin is somewhat irregular. The mycelium is usually white, but can be brownish or pinkish depending on the batch of medium or strain. *Clavaria* mycelium will vigorously grow across the surface of bare glass. It has been seen creeping up the sides of slant tubes and even up the sides and across the tops of glass petri dishes. Contaminants do not show this level of vigor. After long storage in a refrigerator or vigorous growth at room temperature, black shiny droplets will form on the mycelial mat. This has been tentatively identified as polymerized sugar, but samples should be analyzed to confirm this initial identification. *Clavaria* medium turns black after it is colonized. The black compounds could be polymerized sugar or phenolic compounds, but have not been determined at this time.

Contamination has been why *Clavaria* was previously considered unculturable. Actinomycetes, bacteria, fungi, and nematodes have all been troublesome. Bacteria appear as individual colonies on the agar surface within the first 3 days. Actinomycetes, specifically *Streptomyces* spp., resemble streptococcus bacteria under the microscope, but have a larger diameter. They appear as wispy hyphae-like chains on the agar surface and will cover the plate within 3 days. Fungal contamination, predominantly *Aspergillus* spp., has a uniform margin, is appressed to the agar surface, and appears in other spots than the inoculation site. It usually sporulates profusely and often has a dark brown or grayish black mycelium. *Mucor* or a similar fungus is often present and appears like long bushy hairs with small liquid droplets at the tips and growing directly from the section. *Fusarium* spp. produce chlamydospores and have dark hyphae, however it is not common. Numerous other fungal contaminants appear, but good sterile technique eliminates them.

Attempts to control contaminant fungi with Benomyl fungicide in the medium were unsuccessful and produced deformed *Clavaria* mycelia. Banrot did not control *Aspergillus* mold, but *Clavaria* in those plates was too contaminated to differentiate. The effect of Banrot fungicide on *Clavaria* is unknown. It is possible that sterilization rendered the fungicides ineffective. Concentrations were calculated from field recommendations on the pesticide bags and could be in error. Fungal contaminants are best controlled by proper sterile technique.

Mycophagus nematodes are infrequently a problem. As the mycelium grows, the center of the mat, where it was inoculated, appears watersoaked and the margin of the watersoaked area moves to the edges as nematodes multiply. Control of nematodes in culture has been unsuccessful. Oxamyl may be useful in controlling nematodes, but it should be sterile filtered and added to the medium after sterilization. It is volatile and may become ineffective in the sterilization process. Insufficient filter equipment has disallowed this control from being tested. Infested vessels should be separated from clean ones and discarded. Subculturing from infested cultures is not advisable and has been unsuccessful, as only one live nematode is required to repopulate. Nematodes appear to be resistant to sodium hypochlorite and other surface-sterilizing agents such as potassium permanganate. The best control of nematodes is to avoid excess moisture and use freshly harvested basidiocarps in their prime stage.

Subculturing:

*Clavaria pulchra* has been subcultured onto several different media, including PDA, Malt-Peptone-Grain Agar, and even Tryptic Soy Agar. It is a good idea to change media periodically to keep the mycelium vigorous and keep it malleable. Reculturing it onto the same medium every time can make it unable to grow on anything else. All media require the addition of ethanol or corn oil. Good additions are thiamine, yeast extract, and peptone or another N source. More research must be done on the nutrition of the fungus to determine its requirements for other vitamins, nutrients and carbon sources.

Storage:

Cultures have been stored as many as 9 months in sealed slant tubes in a basement at ambient temperature before subculturing. Longest storage so far has been in a refrigerator at 40° F. in sealed petri dishes for 11 months, however this causes too much condensation. Subculturing will be done at one year to confirm viability.

Other Species:

The isolation method mentioned above has been used to isolate *Clavaria pulchra, Clavaria vermiculata, Clavicorona* spp., and an unknown species of *Clavaria* growing on a Pin Cherry log. Modifications to the method are only in the surface sterilization time and the sectioning. Smaller basidiocarps can tolerate only 30 seconds in bleach solution. *Clavicorona* basidiocarps are too small to section, and *Clavaria vermiculata* basidiocarps yield only 1–2 effective sections. The same contaminants have been seen on all species of *Clavaria* and *Clavicorona*.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

What is claimed is:

1. An isolated and biologically pure culture of *Clavaria* fungus.

2. An agricultural composition for plant growth comprising an effective amount of a biologically pure culture of *Clavaria* fungus.

3. A biologically pure mycelium of *Clavaria* fungus.

4. The mycelium of claim 3 wherein the mycelium is derived from a culture or subculture.

* * * * *